US009533064B1

(12) United States Patent
Adiga et al.

(10) Patent No.: US 9,533,064 B1
(45) Date of Patent: Jan. 3, 2017

(54) DEVICE AND METHOD FOR DECONTAMINATION, DISINFECTION, AND SANITATION

(71) Applicants: Kayyani C. Adiga, Macon, GA (US); Robert F. Hatcher, Macon, GA (US); Rajani Adiga, Macon, GA (US)

(72) Inventors: Kayyani C. Adiga, Macon, GA (US); Robert F. Hatcher, Macon, GA (US); Rajani Adiga, Macon, GA (US)

(73) Assignee: Nanomist Systems, LLC, Macon, GA (US)

( * ) Notice: Subject to any disclaimer, the term of this patent is extended or adjusted under 35 U.S.C. 154(b) by 329 days.

(21) Appl. No.: 13/945,897

(22) Filed: Jul. 18, 2013

Related U.S. Application Data

(60) Provisional application No. 61/801,731, filed on Mar. 15, 2013.

(51) Int. Cl.
  *A61L 9/00* (2006.01)
  *A62B 7/08* (2006.01)
  *A61L 2/22* (2006.01)

(52) U.S. Cl.
  CPC ........................................ *A61L 2/22* (2013.01)

(58) Field of Classification Search
  CPC ............... A61L 9/00; A61L 9/015; A61L 9/14
  USPC .................... 422/1, 5, 28, 120, 127
  See application file for complete search history.

(56) References Cited

U.S. PATENT DOCUMENTS

| 7,157,046 | B2 | 1/2007 | McVey et al. |
| 7,354,551 | B2 * | 4/2008 | Mielnik et al. ................. 422/32 |
| 7,361,304 | B2 | 4/2008 | McVey et al. |
| 8,007,717 | B2 | 8/2011 | Hill |
| 8,349,272 | B2 | 1/2013 | Hill |
| 2010/0143189 | A1 | 6/2010 | Martin |

OTHER PUBLICATIONS

K.C. Adiga, Heather D. Willauer, Ramagopal Ananth, Frederick W. Williams, "Implications of droplet breakup and formation of ultra-fine mist in blast Mitigation", Fire Safety J. (in press) Oct. 2008.
Adiga KC, Hatcher Jr. RF, Sheinson RS, Williams FW, Ayers S., A computational and experimental study of ultra-fine water mist as a total flooding agent. Fire Safety J. 2007; 42: 150.
Madjid Birouk, Iskender GoKalp, "Current status of droplet evaporation in turbulent flows", Progress in Energy and Combustion Science 32 (2006) 408-423.

* cited by examiner

*Primary Examiner* — Monzer R Chorbaji
(74) *Attorney, Agent, or Firm* — Brian D. Bellamy

(57) ABSTRACT

A mist generator is used to deliver a high throughput extremely fine mist comprising a biocide. Flows of evaporating hot gas mix turbulently and enhance forced heat and mass transfer between the very fine droplets and the hot gas to form a well-mixed premixed evaporator, resulting in high humidity vapor formation well inside a tube. The high relative humidity vapor with elevated temperature is then condensed as it exits the tube and disperses into the volume to be decontaminated as a condensed vapor cloud, but neither as a mist nor as a pure vapor depending on temperature and humidity of room environment. The condensed vapor cloud may evaporate or settle on the volume surfaces and contents, whereby both dry vapor and condensed vapor are applied into the volume for the killing process.

28 Claims, 8 Drawing Sheets

(1) MIST
- Mirror Temperature, ambient ~22-25 C
- The mirror becomes wet if droplets impact on the surface, irrespective of mirror temperature (2) Already Condensed vapor
- The exit plume from outlet looks hazy/foggy
- Does not collapse on the mirror above dew point (3) Pure Vapor
- The mirror is cooled below dew point
- Microdroplets will condense on the mirror surface, immediately (4) Vapor; not Mist
- The mirror is not cooled below dew point
- Droplets do not collapse on mirror
- Not mist, but vapor

Fig. 5

DEVICE AND METHOD FOR DECONTAMINATION, DISINFECTION, AND SANITATION

CROSS-REFERENCE TO PRIOR APPLICATIONS

The present application claims priority to U.S. Patent Application 61/801,731 filed Mar. 15, 2013, which is incorporated by reference in its entirety.

FIELD OF INVENTION

This invention relates to a device and a method for decontaminating a volume, and more particularly, a method and device for producing low temperature, high throughput condensed vapor clouds of biocide liquids and air using an ultra-fine mist evaporator, and discharging the biocide—air mixture into the environment or volume to be decontaminated. The biocide is deployed as aggregates of a condensed vapor cloud mixture comprising a liquid biocide concentration or composition different from the starting liquid. The condensed vapor cloud, upon exposure to the environment and depending on the humidity and temperature of the environment, may evaporate into vapor or may remain as fine condensed vapor droplets, either of which or a combination of which, can be used for the decontamination of the volume and the contents within it.

BACKGROUND OF THE INVENTION

Background
There is a continuing need for improved methods to decontaminate various volumes and the objects within them both on a small scale, such as instruments within a chamber and on a large scale, such as entire rooms and the objects within. While there have been attempts to develop methods for decontaminating such enclosures from microbial pathogens, chemical agents, odors, and the like, current methods have shortcomings based on their scalability, the long duration of their operating cycles, the cost associated with the equipment, safety concerns and other limitations. With the continuing spread of resistant bacterial pathogens such as MRSA (methicillin-resistant staph *aureus*), c.diff (*clostridium difficile*), viral pathogens such as rotavirus and rhinovirus and other pathogens such as stachybotrys mold, there is a growing need for an effective, economical, rapid method of decontamination. Preferably, in addition to being cost effective, efficacious, and quick, a successful method should be scalable, yet also portable and completely automated to be used in a wide variety of situations with minimal need for reconfiguration.

Hydrogen peroxide and other biocides have been employed in various methods to decontaminate the aforementioned and other contaminants with varying success. While hydrogen peroxide can be an effective decontaminant, challenges exist with deploying it at sufficient concentrations, in sufficient quantities, at a sufficiently rapid rate to be effective, efficient, and adaptable to a wide variety of environments.

Furthermore, the production of condensed vapors of various biocides and neutralizing agents are important for various industrial applications including biodecontamination, sanitation, sterilization, air sterilization, odor removal, factory fumigation, chemical and biological agent neutralization and, use of condensed vapor as a gaseous reagent in gas phase problems.

Brief Discussion of the Prior Art
The prior art teaches various methods for evaporation and vaporization of biocide liquids. These methods include flash vaporization, spray vaporization, and very fine droplet evaporation and drying, among others. Generally, biocide is injected either as a mist, a collection of droplets created through mechanical shearing of the initial liquid, or a vapor, a completely gaseous form of the initial liquid, coming from an apparatus or a device.

Flash Vaporization:
Flash vaporized hydrogen peroxide in biodecontamination processes are taught in U.S. Pat. Nos. 7,014,813; 7,157,046 and 20100143189. In these and many industrial processes, vapors are produced by flash vaporization of solutions or liquid mixtures, or heating of the liquid above its boiling point, on a hot plate or similar massive heat source The vapors are then moved by a carrier gas to discharge them to application areas. Flash vaporization has a number of drawbacks. For example, the vapors are produced above the boiling point and exit with elevated temperatures, the flash vaporization by hot plate and heated blocks is proven to be inefficient in producing large quantity of vapors due to the small surface area per unit of mass of large liquid pools, films, or droplets for heat and mass transfer, and there are severe scaling limitations because of the large-scale heating structures needed to vaporize scalable amount of liquids and thermal inertia problems. The prior art does not teach a methodology of using hydrogen peroxide as a sterilizing agent that would be applicable to the need for an improved method of discharging a condensed vapor or condensed vapor mixture of hydrogen peroxide into the volume to be decontaminated where a concentrated biocide solution might be preferred.

Spray Vaporization and Evaporation:
Another method is spray vaporization and evaporation. U.S. Pat. No. 7,354,551, and U.S. Pat. No. 8,007,717 describe two-phase mixing of spray with hot gas to produce vapor. The vapor is produced by spray vaporization of liquid droplets. The droplets are plunged into a high velocity gas stream or, alternatively, high velocity spray droplets are discharged into a relatively still air environment. The ability to generate a sufficiently high concentration of vapors will depend on the efficiency of evaporation, rather than just the availability of heat or enthalpy for evaporation. The extent and rate of evaporation depends on the droplet size and its size distribution, the number density of droplets, the relative velocities of the air and the droplets, the thermal environment and the humidity conditions. The key to successful evaporation of all the droplets depends on how the droplets interact with the forced convection flow, turbulence, and the rate at which heat and mass is exchanged across the interface.

The most important factor is the surface to volume ratio of droplets followed by its entrainment, turbulence and mixing. Small (less than 10-20 micron) droplets, preferable monodisperse, have a huge surface to volume ratio yielding efficient heat and mass transfer. The local humidity surrounding the individual droplets is also an important factor.

In summary, the prior art methods of producing vapors from liquid systems by spray drying and forced convective evaporation have several shortcomings in an application that requires very rapid and complete evaporation of large quantities of input liquid. The use of sprays to produce the droplets for evaporation involves a wide range of droplet sizes. The larger the droplets, the higher the heat and mass transfer rate requirement in order to completely evaporate the droplets. Thus, the larger droplet sizes associated with the broad droplet size distribution found in most spray systems will not completely evaporate in acceptably short timescales. This renders the system costly and not scalable for large scale vapor production for commercial applications. Furthermore, to solve this problem of larger droplets within the droplet size distribution, spray systems will require increasing amounts of pressure to create finer droplets to avoid long evaporation time scales. This pressure, and the sudden release of this high pressure at the nozzle orifice, can have detrimental effects on various chemical components of biocides to be vaporized and may pose safety concerns. Further, spray nozzles are subject to erosion, clogging and other such problems that can cause inconsistencies in the output droplet sizes which, as is clearly shown above, will have tremendous detrimental impact on the vaporization process. The prior art does not teach a methodology of using hydrogen peroxide as a sterilizing agent that would be applicable to the need for an improved method of creating a monodisperse mist to provide efficient, complete evaporation of a solution in order to subsequently discharge a condensed vapor or condensed vapor mixture of hydrogen peroxide into the volume to be decontaminated where a concentrated biocide solution might be preferred.

Diffusion Mixing Evaporator:

In US patent 2012/125197, a diffusion evaporation process is disclosed. In this process, the fine mist and the hot air mix only beyond the exit opening of the apparatus to the environment; not inside the apparatus. In diffusion evaporation, heat energy in a hot gas passes through an annular space without contacting, pre-heating, or mixing with the mist until they meet beyond the outlet. Just beyond the exit of the apparatus the mist mixes with hot air and subsequently evaporates in the environment. Because the heating of the mist does not occur until the two streams reach the environment outside of the device, the enthalpy associated with the hot air stream dissipates into the environment decreasing the efficiency of the evaporation process considerably. The '197 publication does not include a methodology of using hydrogen peroxide as a sterilizing agent that would be applicable to the need for an improved method of utilizing rapid, enhanced residence time, premixed evaporation of a solution within the device to avoid the loss of efficiency associated with evaporation outside of the device. The '197 publication does not include a methodology to discharge a condensed vapor or condensed vapor mixture of hydrogen peroxide into the volume to be decontaminated where a concentrated biocide solution might be preferred.

Premixed Evaporation Method:

According to the present invention of premixed evaporator method, a fine mist is entrained into a hot air stream at the base of an evaporator tube and the two are premixed before the efficient evaporation takes place. It is beneficial to create a "premixed" gas and mist droplet zone where residence time is long enough and number density is dilute enough to accomplish instantaneous evaporation of the microdroplets. Entrainment of fine droplets into a hot gas stream is the determining factor in the U.S. Pat. No. 7,090, 028 disclosures by Adiga et al.

Aerosol containing extremely fine droplets of water, those having diameters of less than 10 microns, behaves like a gas or is a pseudo gas, as further described in K. C. Adiga, Fire & Safety Magazine Spring 2007. The evaporation/drying in a premixed system containing such a fine droplet aerosol and the drying gas inside a dryer tube was reported in U.S. Pat. Nos. 7,724,442 and 7,744,786. These patents teach the premixing of a slow moving ultrafine mist of water containing a dissolved solute premixed with a drying gas, such as hot air, with a high enough residence time due to swirling flow. A "premixed" evaporator was disclosed for producing nanoparticles through drying and rejecting the solvent vapor. Adiga describes the drying and evaporation of liquids at low temperature using a swirl flow tube. Although it contains solute additives, the major phenomenon is the efficient evaporation of liquid within the tube. Applications requiring a fast and complete evaporation of droplets require an efficient way of supplying both the proper thermal environment and adequate mixing of the extremely fine droplets within the evaporation volume. While forced convection helps the rate via enhanced heat and mass transfer across the surface, this alone does not guarantee the droplet entrainment into the air, mixing by turbulence and subsequent heat and mass transfer processes. Beyond these, the limiting factor is the number density of droplets that controls the local humidity around individual droplets. At high enough local relative humidity immediately adjacent to the droplet, the evaporation rate falls. To improve the evaporation process will require high temperatures to raise the saturation level of the locally humid air. Any discussion of humidity in this disclosure is purely related to the function of drying the solid and had no bearing on the discharged vapor or its use. In this disclosure, Adiga ignores the vapor and focuses on the dried particles which are collected as manufactured materials. While the disclosed invention does address the heat and mass transfer of evaporation, Adiga does not include a methodology of using a multicomponent liquid-liquid solution without a solid solute included, since this would have no value in creating particles.

A method is needed to provide an efficient mist evaporation process and device producing relatively low temperature vapors which can condense and form concentrated condensed vapor upon coming in contact with cooler air with a potential for seamless scaling capability. Providing a premixed evaporator is an industrially important concept for generating large quantity of completely vaporized premixed mist and warm/hot air system, which can be discharged as condensed vapor cloud, vapor or a mixture.

SUMMARY OF THE PRESENT INVENTION

Accordingly, the overall objective of this invention is to provide a method and device for efficiently premixing warm air and ultrafine biocide mist to form a condensed vapor cloud which is then dispersed into a volume. The warm air and ultrafine biocide are instantaneously evaporated and produce a large quantity of low temperature vapors from ultra-fine mist of single or multicomponent biocide or other liquids without heating them to their boiling points. Using high humidity combined with a reasonably elevated temperature, relative to the environment of the volume where dispersed, vapor is produced inside an evaporator tube/drying tube/device and when it is mixed with cooler air, such as when it is discharged into the environment of the volume to be decontaminated, it forms a condensed vapor cloud. According to this invention a condensed vapor cloud of the biocide is dispersed into the volume to be decontaminated. Depending on the room temperature and room air humidity, the condensed vapor cloud discharged may "re-evaporate" and become vapor or may remain condensed vapor (liquid droplets) or may partially evaporate creating a mixture of vapor and condensed vapor. Further, the condensed vapor cloud discharged will contain a much higher concentration of the biocide within the liquid solution in each droplet than the original low concentration biocide because the high boiling point (high vapor pressure) liquid component concentrates in the condensed phase. The process parameters can be varied, including initial room temperature and humidity, to manipulate the condensed vapor cloud such that it may later become pure vapor, condensed vapor, or some mixture thereof. In one embodiment, a secondary cooler air inlet may be installed downstream of the vapor zone inside the tube, prior to its exit into the room. This cool air will enhance the condensed vapor formation within the tube and at the exit via lower dew point.

It is another objective of this invention to avoid detrimental thermal impact to the chemistry of the input components by avoiding excessive heat in the evaporation process, as encountered in the hot plate flash vaporization process.

It is another objective to use nearly "monodisperse" ultrafine mist droplets of multicomponent liquids that are produced from a source such as an ultrasonic atomization device so that the mist-to-vapor conversion rate is very high and efficient.

It is another objective of this invention to evaporate a relatively dilute biocide solution and generate condensed vapor liquid droplets richer in biocide components.

It is another objective to vary the configuration of the vapor discharge port or ports to facilitate high dispersion efficiency of the condensed vapor cloud formed upon discharge.

It is another objective to provide various heating sources for the evaporating gas (air) such as, but not limited to, electrical energy, fuel combustion, inductive heating, microwave, laser heating, or exothermic chemical systems for augmenting energy.

It is a further objective to generate a general principle for combining mist and hot air streams to facilitate efficient mixing and evaporation such that those who are skilled in the art may devise designs that incorporate co-flows, opposing flows, and shearing flows with widely varying flow angles.

Another objective of this invention is to modify and extend the prior art design and the prior art process to generate energy efficient large scale premixed vapors from ultra-fine mist of biocides which includes aqueous hydrogen peroxide (HP) of various concentrations and several other liquids which will be described later.

BRIEF DESCRIPTION OF THE FIGURES

FIG. 5 is a schematic view illustrating a preferred embodiment of the evaporator-vapor cloud discharge apparatus with two hot air gas inlets on either side;

DEFINITIONS

Figure 1:
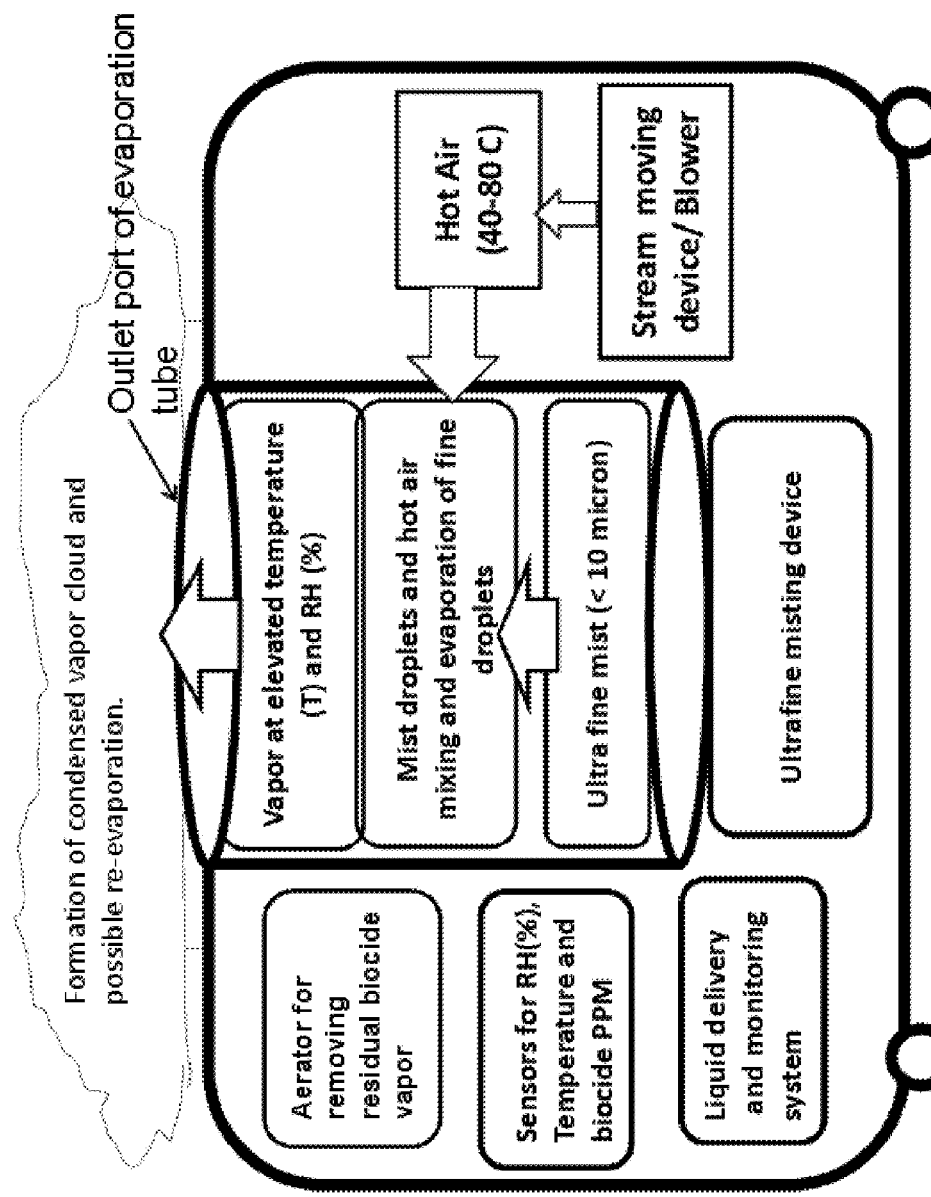
FIG. 1 is a flow chart describing the various physical and transport processes occurring in the decontamination apparatus and the decontaminating environment or room.

The following terms are defined as follows for the purposes of this disclosure:

"Mist" broadly refers to the microdroplets of liquid dispersed in gas or air which is also called an aerosol. It can be produced by various means of shearing force to create the micro droplets such as ultrasonic atomization, pressure jet atomization, or electrostatic atomization, among others. The composition of each droplet, if multi-component, is generally similar to the virgin liquid when formed through mechanical shearing except in some cases of ultrasonic atomization.

"Vapor" is the pure gaseous form of a liquid in equilibrium with liquid, below its saturation vapor pressure, or dew point.

"Premixed evaporation" broadly refers to the conditions wherein the evaporating gas (warm or hot air) and a low momentum, or velocity, ultra-fine mist are premixed and vaporized completely inside dryer tube within a short distance. The product is discharged as pure vapor, condensed vapor or mixture thereof.

"Condensed vapor" generally refers to liquid droplets formed from saturated vapors on surfaces such as in the form of thin films, microdroplets, or pools. In this disclosure condensed vapor is vapor condensed to form droplets in air or other gaseous carrier when the vapor reaches its saturation vapor pressure and the temperature drops below the dew point.

One characteristic of condensed vapor droplets or films formed from a multicomponent biocide is that they may have a different concentration from the virgin liquid depending on the relative boiling points, or vapor pressure, of the multiple components. For example, aqueous hydrogen peroxide solution with a starting composition of 5% by wt upon evaporation and condensation will have much higher hydrogen peroxide concentration in condensed liquid form. The liquid will be richer in the higher boiling point component of the fluid (HP).

"Cloud" or "condensed vapor cloud" refers to a mixture of high humidity gas and condensed liquid droplets.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

The terms "a", "an", and "the" refer to "one or more" when used in the subject specification, including the claims. Thus, for example, reference to "a particle" includes a plurality of such particles, and so forth.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter As used herein, the term "about", when referring to a value or to an amount of mass, weight, time, volume, concentration, or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

All compositional percentages used herein are presented on a "by weight" basis, unless designated otherwise.

DETAILED DESCRIPTION OF THE INVENTION

The following description is intended to provide the reader with a better understanding of the invention. The description is not intended to be limiting with respect to any element not otherwise limited within the claims.

The present invention discloses a short length evaporation process that focuses on the resultant vapor as a means of producing a desired and optimized output in the form of a condensed vapor cloud discharged into an environment to be decontaminated, preferably a room or an enclosed volume for decontamination, disinfection or sanitation.

FIG. 1 shows a flow chart of the present inventive method for producing a condensed vapor cloud for decontamination of a volume and its contents. In a preferred embodiment, monodisperse ultrafine mist of a biocide or other solution is produced using an ultrasonic or suitable atomizer device and carried to the inlet of the evaporator enclosure. Separately, an air movement device is used to transport a gas through a heating device to warm the gas stream to be used as evaporating gas. The ultrafine mist and evaporating hot gas stream are introduced into the evaporator enclosure where they are premixed.

The premixed mist-gas mixture is subjected to turbulent mixing accompanied by enhanced heat. Heat and mass transfer between extremely fine sized droplets and hot gas produces completely evaporated, relatively low temperature vapors inside an evaporation/drying tube within a short distance downstream. The details of heat and mass transfer are provided in subsequent sections. The evaporation distance is shortened through enhanced residence time fluid mixing facilitated via swirling flows that meet normal to each other in the base of the tube. The evaporated vapors have now relatively low temperatures and high relative humidity, preferably close to or at saturation. Upon exiting from the tube and mixing with low humidity, low temperature room air, the vapors coming from inside the tube form a condensed vapor cloud. The density and extent of cloud will depend on the relative humidity (RH) and temperature of vapors formed by the premixed evaporation relative to the RH and temperature of the environmental air immediately next to the exit. In summary, the present method discharges a vaporous cloud containing sub-micron and micron scale droplets of condensed vapor containing concentrated biocide or other liquid. The condensed vapor cloud will subsequently disperse throughout the space as ultra-fine or extremely small condensed vapor droplets with higher biocide concentration in each compared to the lower concentration initial solution or will evaporate again to become pure vapor in the case of low environmental RH and disperse throughout the volume. Further, some proportion of condensed vapor and evaporated vapor may disperse throughout the volume. The conditions of the environment may be manipulated to achieve the desired outcome. The discharge stream may be manipulated to provide controlled portions of components of pure vapor, and nano and sub-micron droplets of the mist in addition to the condensed vapor cloud, whereby additional applications are provided.

Referring to FIG. 1, the flow chart also shows exemplary components of the decontamination system disclosed herein. Additional components to the core system discussed above include a liquid delivery system, sensors for RH, biocide, and temperature, a terminal biocide cleaning device, and a catalyst aerator. These components are shown in the left part of the flow chart diagram and included to provide context for the present invention, while not necessarily specifically required to practice each embodiment discussed.

Figure 2:
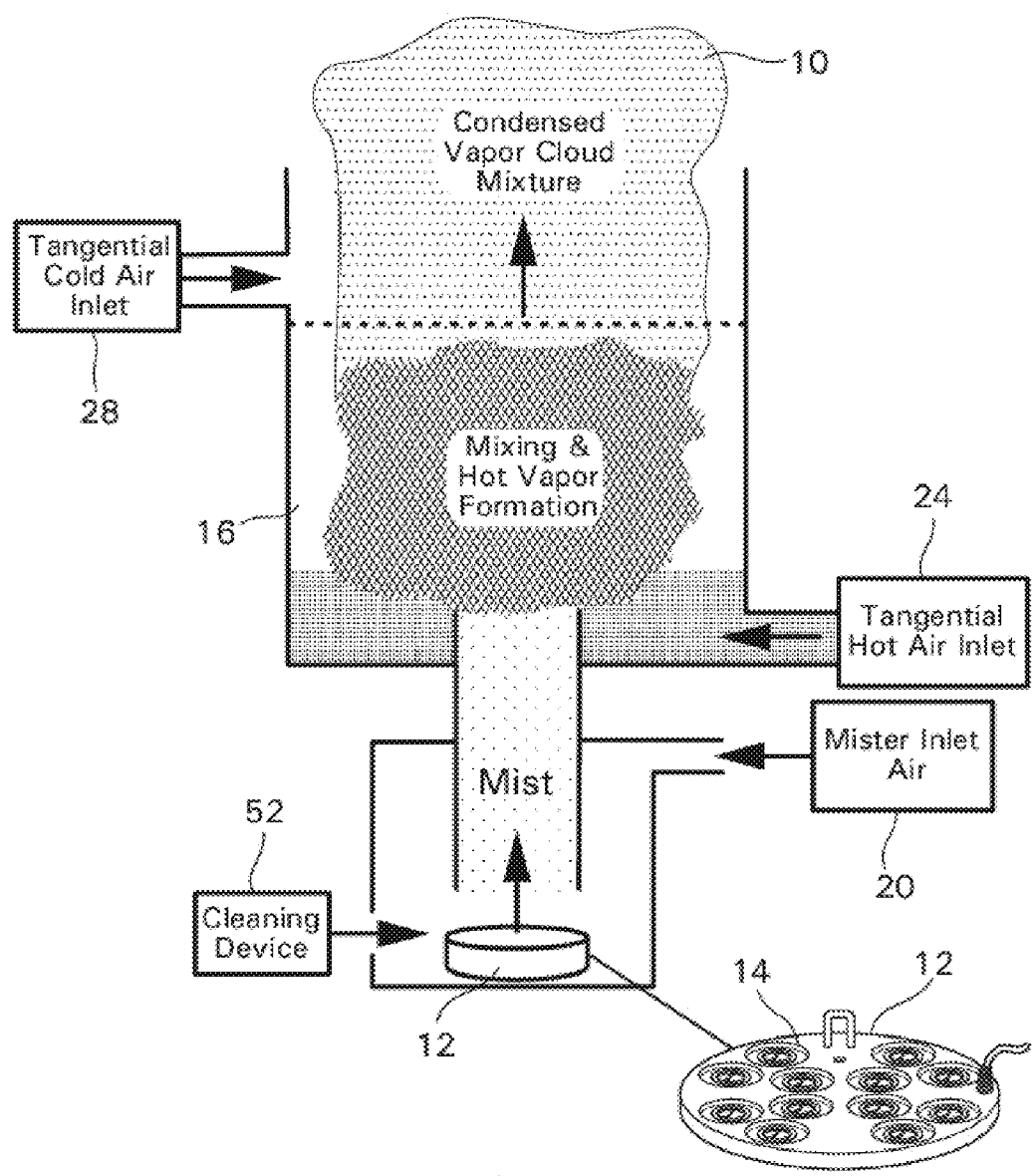
FIG. 2 is a schematic view of a biocide evaporator producing condensed vapor mixture at the outlet port.

As shown in FIG. 2, a condensed vapor cloud 10 is produced when a mist is generated from an ultrasonic mist generating disc 12, then fed to an evaporator enclosure 16 where it is mixed with hot air. In a preferred embodiment, the mist produced is extremely fine, with particle diameters of less than about 10 microns. Further in a preferred embodiment, an extractor is used to produce and select a spectrum of very fine mist size with low enough momentum, as in U.S. Pat. No. 6,883,724 and U.S. Pat. No. 7,264,773, both to Adiga et al. The mist is fed into the evaporator enclosure 16. The low momentum and extremely fine droplet size results in almost molecular level mixing. Large droplets, as seen in usual high pressure atomizers nozzles, will not tend to premix with hot air. Rather, they form a diffusional transport system with very low evaporation efficiency. Alternatively, the ultra-fine mist may be produced using electrostatic methods, pressure-ultrasonic methods and other means known in the art for producing extremely fine mists. Any suitable means of producing a monodisperse ultra-fine mist may be used in accordance with the preferred embodiments disclosed. Mist throughput can be increased up to 80 g/min for water and 60-70 g/min for 35% hydrogen peroxide solution. However, the ability to evaporate, for example, a 35% HP solution may be limited to heat energy available. In a preferred embodiment, up to 50 g/min is vaporized to get condensed vapor at the outlet of the evaporator device.

An exemplary ultrasonic disk 12 has multiple misting jets containing 1-5 mm recesses or dips. Typically in a 12-jet misting disk, as shown in FIG. 2, there are twelve recesses 14 formed by the housings of the embedded Piezo crystals.

After misting, a portion of the solution typically remains in the recessions on the crystals. In order to ensure the safe removal of biocide content in the apparatus, the remaining solution may be evaporated and exhausted out of the device into the room. 2A hot air blower cleaning device 52 discharges warm, high-speed air to evaporate the remaining biocide and exhaust it from the ultrasonic mist generating disc 12. After each misting event, the hot blower 52 is activated and the air blows out the solution leftover on the recesses 14 and evaporates it. This action ensures that the apparatus is clean, dry, and safe for handling before the next application. The hot air cleaning sequence can be done after misting, but before starting the aeration process or well into aeration process.

A mister air inlet 20 provides an air flow to move the mist to the evaporator enclosure 16 where the mist is mixed with an evaporating gas to produce a premixed evaporation. The evaporating gas may be heated and may be provided via a tangential hot air inlet 24. In one embodiment, before exiting the evaporator enclosure 16, the premixed evaporation is combined with a secondary supply of cooler air supplied through a secondary air inlet 28. When the premixed evaporation is mixed with cooler air, the condensation and condensed droplet concentration at and just beyond the exit of the evaporator enclosure 16 can be controlled.

Preferably, the mixing region within the evaporator enclosure 16 is very short because of extremely small droplets, intimate mixing, and the enhanced residence time afforded by the swirling flow. Should a longer evaporation path be desired, the evaporation tube of the enclosure shown in FIG. 2 can turn to horizontal using a 90 deg. elbow and then turn back upwards. Other such variations in evaporator configuration can be made without departing from the spirit of the present invention.

The relationship below describes the evaporation time (inverse of evaporation rate) for a single droplet. Various parameters influencing the evaporation rate are listed. As can be clearly seen, beside the initial droplet diameter, the humidity around the droplet is very important.

The evaporation time of a single droplet of water:

$$t_{vap} = \frac{d_{in\,initial}^2 \rho_l}{8\Gamma_{vap}\ln\left(1 + \frac{m_{vap,o} - m_{vap,\infty}}{1 - m_{vap,o}}\right)} \quad (1)$$

Where:
$t_{vap}$=evaporation time (s)
$d_{initial}$=initial diameter of the droplet (m)
$\rho_l$=liquid water density=1000 kg/m$^3$
$\Gamma_{vap}$=water vapor exchange coefficient (kg/m·s)=2.6×10$^{-5}$ kg/m·s
$\Gamma$=exchange coefficient=D$\rho$(D=vapor diffusion coefficient (m$^2$/s), $\rho$=vapor density (kg/m$^3$)
$m_{vap,o}$=mass fraction of water vapor in the mixture at temperature T(K) at the droplet surface.
$M_{vap,\infty}$=mass fraction of water vapor away from surface at temperature T(K).

In this example, the relative humidity, RH=0 (dry air). $m_{vap,\infty}$=0.

Figure 3:
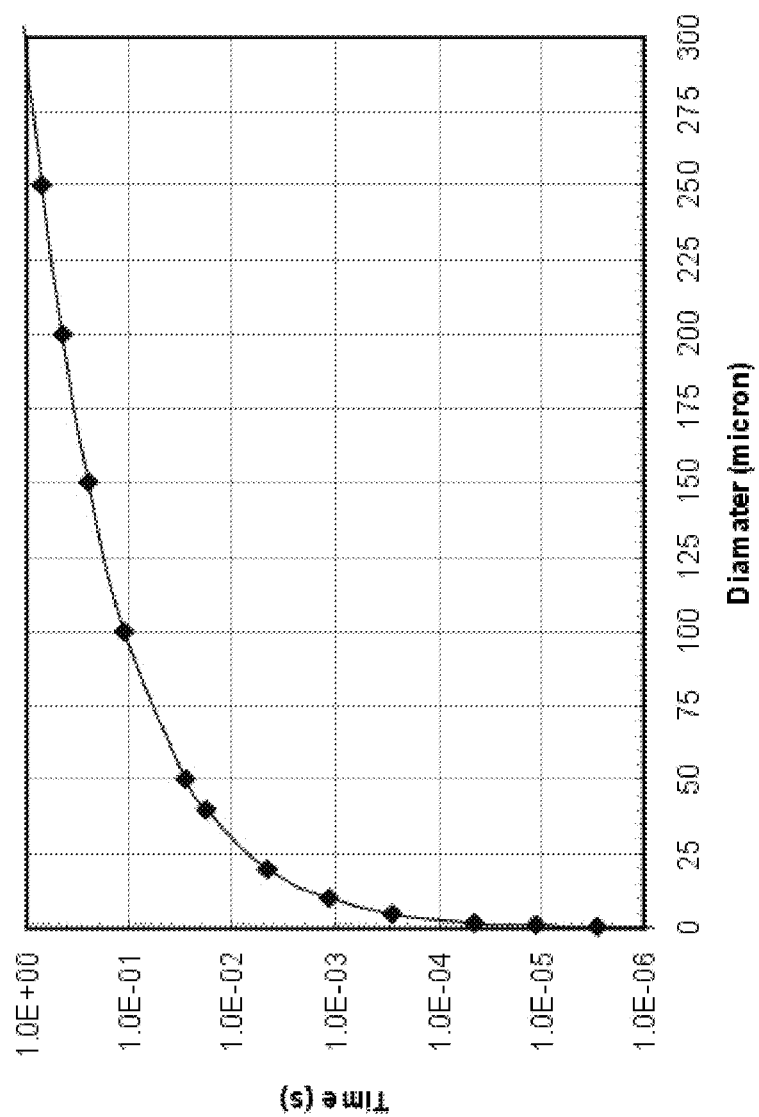
FIG. 3 is a chart illustrating the evaporation behavior of ultrafine mist droplets used in preferred embodiments of the present invention.

For exemplary purposes only, FIG. 3 shows the variation of droplet vaporization time as a function of droplet diameter at 80° C. if the relative humidity (RH) is zero. Note that the droplet vaporization time scale starts at microseconds and ends in seconds for droplet sizes associated with sprays. For droplets with diameters of from 1 micron to 5 microns, typical of ultrasonic mist droplets of this invention, the evaporation time is less than a millisecond. However, evaporation times of typical spray droplets having diameters of 100-250 microns extend beyond one second. At evaporation times as short as milliseconds, the process conforms to timescales of flash evaporation carried out above boiling point. Because this rapid evaporation occurs at low temperatures, the chances for distillation of components in binary and multi-component droplets, such as ethanol-water and water-hydrogen-peroxide solutions, is reduced. This is an important consideration in the evaporation of mist droplets for decontamination, sterilization, odor removal, chemical and biological neutralization process by vapors. The forced convection velocity helps to enhance the heat and mass transfer across the droplet-fluid interface and dispersion of the vapor. Assuming a predominantly forced-convective heat transfer from the environment to the droplet in flight, the averaged heat-and-mass transfer coefficients are determined using the Nusselt number, the Sherwood number and the Reynolds number, wherein.

the Nusselt number is determined by:

Nu=2+0.6×Re$_d^{0.5}$Pr$^{0.33}$ the Sherwood number is determined by:

Sh=2+0.6Re$_d^{0.5}$Sc$^{0.33}$ and the Reynolds number is determined by:

$$Re_d = \frac{D_d \times \Delta U \times \rho_a}{\mu_a}$$

As the velocity, and hence Reynolds number, decreases to zero, the transfer coefficients Nu and Sh are then those for molecular diffusion and equal to 2.

Figure 4:
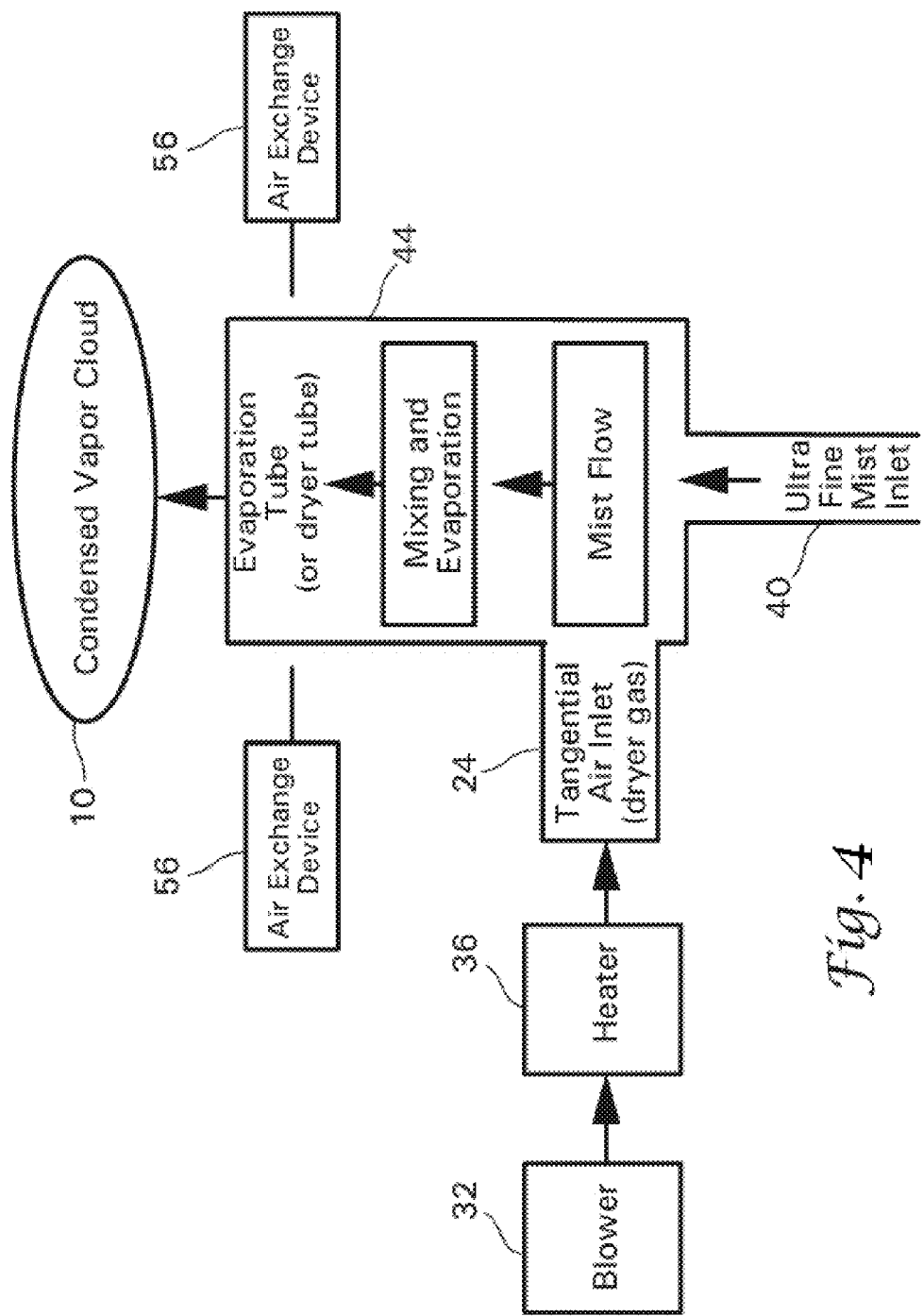
FIG. 4 is a schematic view of the evaporator-vapor cloud discharge apparatus of the present invention with one port of hot air introduction.

FIG. 4 shows the detailed design of a gas heating mechanism and the how the hot gas stream along with air movement device, shown as blower 32 might be connected to the central dryer, evaporator, or tube 44. As shown, an air movement device, blower 32, supplies the evaporation gas to a heater 36. The heated evaporation gas is conducted to the evaporation tube or dryer tube 44 at or near the base of the tube of the evaporator enclosure 16, preferably in a tangential fashion, but in other embodiments may be connected at normal or at various angles. The mist enters the evaporator enclosure 16 after being generated by suitable means via the mist inlet 40 and then evaporated by controlled turbulent mixing with the evaporation gas while resident in the evaporation tube 44 of the evaporator enclosure 16. Adjacent to the outlet of the evaporation tube, there may be multiple air exchange devices 56, which may comprise blowers, to assist vapor distribution throughout the room. These blowers do not directly interact with the rising plumes of condensed vapor but re-distribute the air below the outlet. Their function is to provide additional air exchange for volumes with complicated geometries so that vapors can reach non-line-of-site locations. The outlet of the air exchange devices may be equipped with a method to adjust the directional flow of their output using proper controls.

Figure 5:
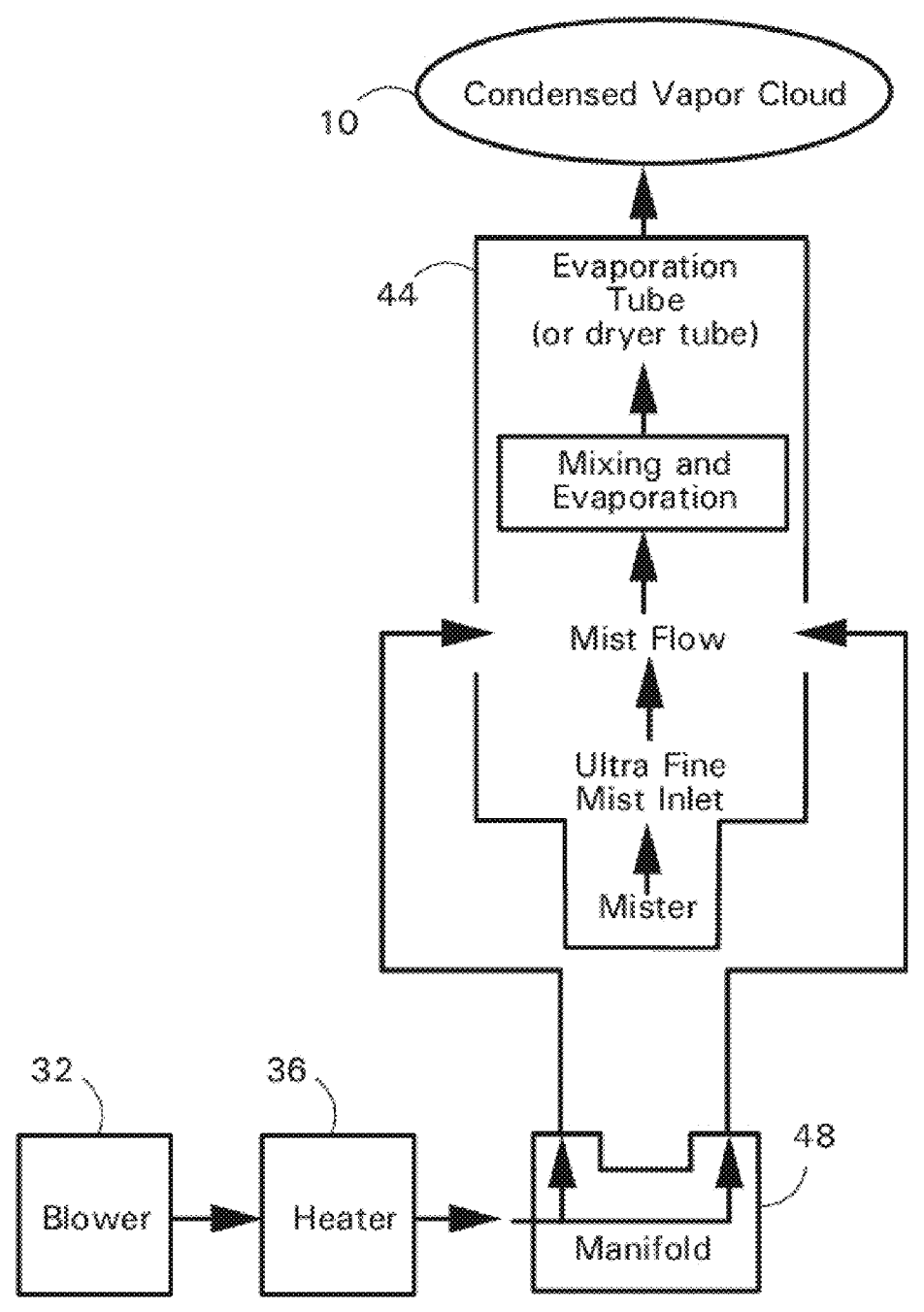

FIG. 5 shows, in a preferred embodiment, a similar heating mechanism installed on two sides of the evaporator tube in order to balance the hot gas flow pattern providing an environment for an enhanced mixing and evaporation process. The inlets 24 are shown as tangential and are attached on two opposed sides, but they might be introduced to the central evaporation tube 44 in a variety of appropriate fashions. Similar to the single entry example in FIG. 5, the heated gas may be provided and moved via a blower 32 and heater 36. A manifold 48 may be incorporated to divide the stream into two and direct the stream of gas to the two sides of the evaporation tube 44.

Figure 6:
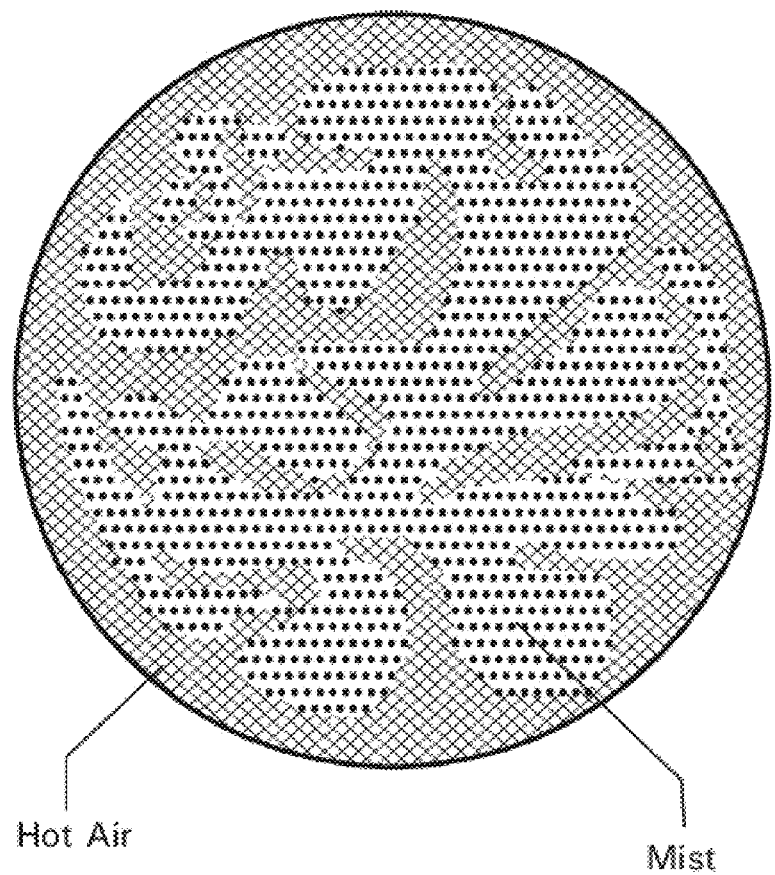
FIG. 6 is a top view of mist and air mixing and evaporation.

FIG. 6 shows a top view of a mixing pattern of the two streams; ultrafine mist and hot air stream. The mixing is efficient because of the level and scale of turbulence and swirling flow. This "premixed" nature of the two streams enhances the forced convection heat and mass transfer between the micro droplets and surrounding air.

Figure 7:
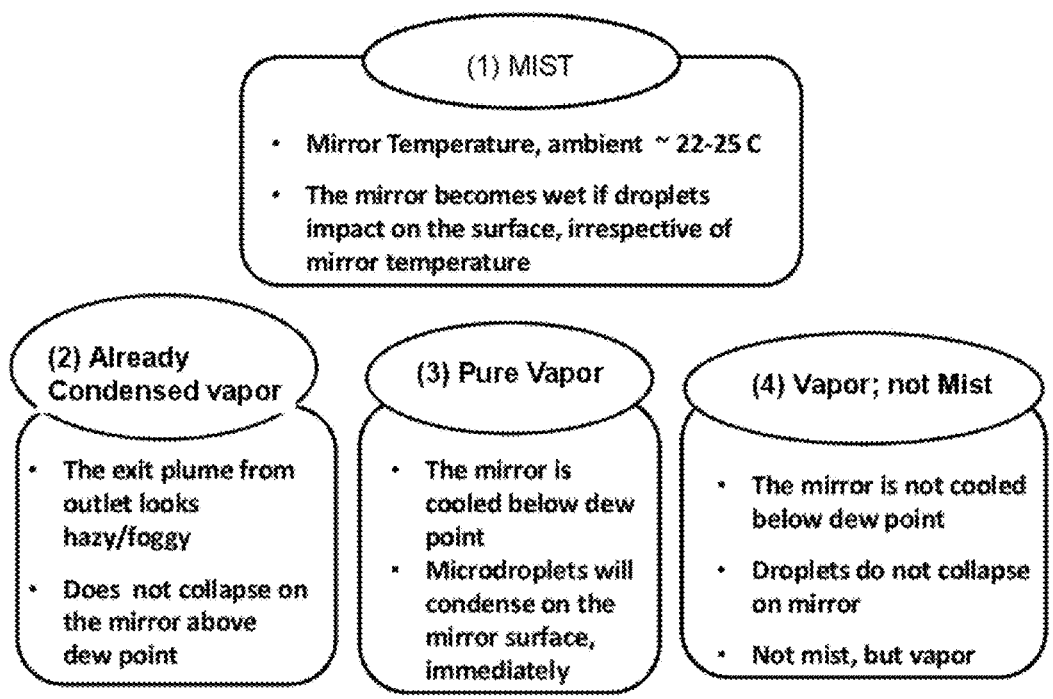
FIG. 7 is a chart illustrating results of a test to confirm if the exit plume flow from the evaporator-vapor cloud discharge apparatus of the present invention is mist, condensed vapor or vapor; and, FIG. 8 is a graph illustrating the relationship of relative humidity (RH %), temperature, and dew point for a condensed vapor cloud example test in accordance with a method of the invention.

FIG. 7 shows a comprehensive test (thermodynamically well accepted) methodology for distinguishing and determining whether the product at the outlet is: 1) virgin mist, 2) condensed vapor, or 3) pure vapor. The tests involve holding a small mirror about 6-inches above the outlet of the device. The mirror is held normal to the flow. In the case of mist, effluent is clearly visible and will collapse, coagulate, deposit and spread on the mirror regardless of the mirror temperature relative to the dew point. In the case of a condensed vapor cloud, the plume will appear hazy/foggy and will not deposit on mirror when it is above the dew point temperature. In the case of pure vapor, the plume will be invisible and it will condense on the mirror which is below the dew point, but it will not deposit on the mirror which is above the dew point.

Figure 8:
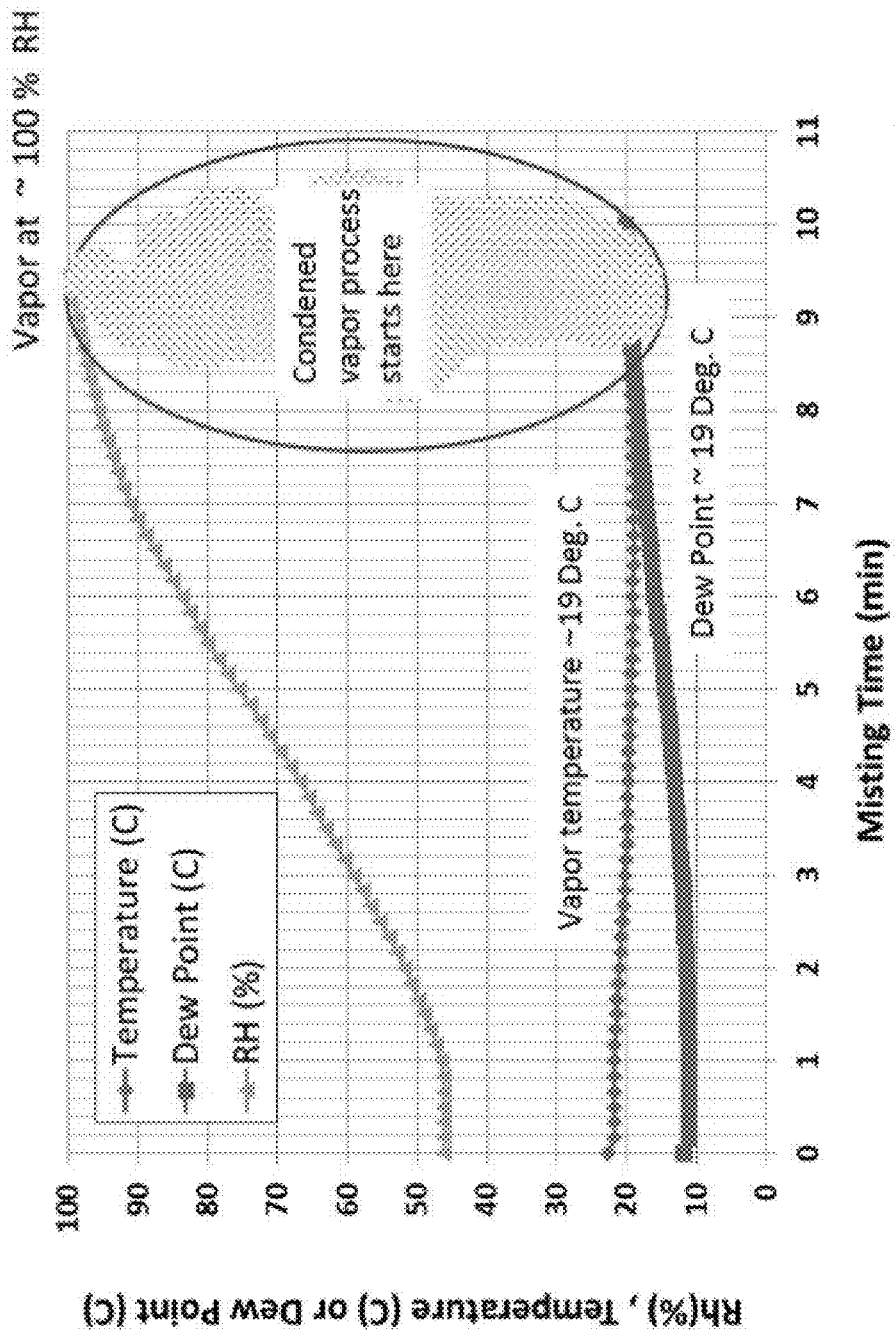

FIG. 8 shows the relative humidity (RH, %) and temperature inside a decontamination room during the misting and vapor formation process. As expected, the RH increases. The temperature slightly increases because of gas/air heating process.

Besides the embodiments indicated above on the mist stream and hot gas, and how they meet and mix, there are several configurations possible with different embodiments. For example, in one embodiment, the introduction of mist and hot air can be switched. Referring to FIG. 2, the mist can enter through the normal or tangential inlet (where hot gas enters) and hot gas can come from the base of the aerator tube. Moreover, those who are skilled in the art can make several changes to the orientation of the entry angles of mist and hot air including partially premixed mist and hot gas in several places. The present invention affords a method to carefully control all of the necessary parameters to suit the particular input liquid characteristics, desired output vapor temperature, desired output vapor concentration and desired evaporation time scales. By varying the relative velocities of the two streams (mist and evaporating gas) the role of convective force in the evaporation process is enhanced or diminished.

In another embodiment, by varying the residence time, evaporation length, and temperature/enthalpy of the evaporating air, the role of heat is enhanced or diminished in the evaporation process. The droplet size and droplet number density can be varied. The discharged stream at the outlet port, in its form as a condensed vapor cloud may also contain extremely small droplets such as nano and sub-micron droplets which have several additional applications.

By varying the volume of evaporating gas, and the expansion of the mixing mist and evaporating gas at the outlet the number density and localized background humidity at the droplet level can be controlled to enhance or diminish the role of this parameter in the evaporation process.

In terms of flow configurations for mist and air pre-mixing and undergoing heat and mass transfer processes, there are other configurations as well. The embodiments described in the present invention indicate the distinguishing features of this invention for low temperature evaporation. They include: 1) huge surface/volume ratio of nearly monodisperse ultra-fine (<10-20 micron) droplets, 2) efficient and adequate heat and mass transfer by warm or ambient air at temperatures far below the boiling point of the liquids rather than heated block thermal storage encountered in flash evaporators, 3) the unique pre-mixing of two stream flow configuration gives ample opportunities to align the streams of mist and evaporating air to improve the mist-droplet entrainment, turbulent mixing and enhance heat and mass transfer between droplet surface and surrounding gas, 4) fine control of number density and local humidity, and 5) guaranteeing flash evaporation to produce high throughput vapors due to shortest time scale of evaporation. The liquid and multicomponent liquid mixtures to be evaporated may include, but are not limited to water, and miscible solutions of water and alcohols, biocides such as hydrogen peroxide, organic compounds and mixtures, oils and their blends, fuels such as petroleum distillates and blends (e.g., kerosene).

The application of condensed vapor cloud generated biocide dispersion was tested in a 36-m$^3$ single room and in 110-m$^3$ two-room model (family room+bathroom). The single room was tiled floor and two-room model had wall-to-wall carpet. With initial room humidity in the range 40-55% RH and 20-25 C, decontamination tests were carried out using biological indicators (BI). Biological indicator test disks were prepared by Mesa Labs. The Biological indicators are inoculated with 4-log, 5-log and 6-log populations of *G. Stearothermophilus*. The BI's are in Tyvek pouches. The hydrogen peroxide vapor concentration was measured by both high range (0-1000 PPM) and low range (0-10 PPM) sensors from ATI (Analytical Technology Incorporated). Both in 36-m$^3$ room and 110-m$^3$ carpeted rooms 5-log kills were observed above 0.7 g/m$^3$ of HP concentration and 6-log kill was observed above 1.8 g/m$^3$. The kill time was 10-15 min at HP mass injection rate of ~50 g/min. The condensed vapor generator was calibrated with scaling of room size, mass concentration, carpet/tilled floor, and initial RH and temperature.

While specific embodiments are described in the present disclosure, those who are skilled in the art may make various other changes and modifications without departing from the true spirit and scope of present invention. We intend to cover all such changes in our claims listed below which are within the scope of current disclosure.

Specific dimensions relevant to the decontamination device are provided herein for the purpose of demonstrating the invention, but these dimensions are not intended to limit the scope of the invention. It is understood that one skilled in the art may make alterations to the embodiments shown and described herein without departing from the scope of the invention.

What is claimed is:

1. A method for decontaminating a volume and its contents comprising the steps of:
    a. generating a mist of ultrafine droplets comprised of a biocide solution;
    b. generating an evaporation gas;
    c. mixing the mist with the evaporation gas in an evaporator enclosure and providing a residence time sufficient to evaporate the mist;
    d. producing a vapor inside the evaporator enclosure from the evaporated mist;
    e. condensing a proportion of the vapor after discharge from an exit of the evaporator enclosure and forming a condensed vapor cloud; and
    f. dispersing the condensed vapor cloud throughout the volume to be decontaminated.

2. The method of claim 1 wherein the step of generating the evaporation gas further includes warming the evaporation gas.

3. The method of claim 2 wherein the evaporation gas is warmed by an electric heater, inductive heater, laser, microwaves, fuel combustion, exothermic chemical systems, or combinations thereof.

4. The method of claim 2 wherein the evaporation gas is heated to a temperature of up to 150 degrees C.

5. The method of claim 1 wherein the step of generating the mist further includes introducing into the evaporator enclosure a mist comprising up to 50 g/min of 35% hydrogen peroxide solution from 1.8 to 2 kW of heat energy.

6. The method of claim 5 wherein the step of heating the mist by the evaporation gas in an evaporator enclosure with the appropriate residence time to evaporate the mist includes controlling the residence time, controlling the mist's length of evaporation time, controlling temperature and enthalpy of the evaporation gas, and controlling mist's droplet size and droplet number density, whereby heat involved in the evaporation process is enhanced or diminished.

7. The method of claim 1 wherein the mist and the evaporation gas are premixed to form a premixed mixture.

8. The method of claim 1 including the additional step of forming a biocide concentration level in an environment of the volume and continuing the step of dispersing the condensed vapor cloud throughout the volume to be decontaminated until the biocide concentration level in the environment is sufficient to decontaminate the environment.

9. The method of claim 1 wherein during the step of dispersing the condensed vapor cloud throughout the volume to be decontaminated the condensed vapor cloud evaporates.

10. The method of claim 9 wherein said condensed vapor cloud partially evaporates and partially remains a condensed vapor cloud.

11. The method of claim 1 wherein said condensed vapor cloud comprises a higher biocide concentration than the biocide solution.

12. The method of claim 1 wherein after the step d), a secondary source of air is provided that is relatively cooler than the vapor for controlling condensation and condensed droplet concentration at and just below the exit of the evaporator enclosure.

13. The method of claim 1 wherein after the step d), a portion of the vapor is condensed downstream of where vapor is produced within the evaporator enclosure to form a portion of the condensed vapor cloud prior to discharge of the vapor from the exit.

14. The method of claim 1 wherein the step of condensing a portion of the vapor within the evaporator enclosure includes introducing a source of cool air downstream of where vapor is produced within the evaporator enclosure.

15. The method of claim 1 wherein said mist of ultrafine droplets is generally monodisperse.

16. The method of claim 1 wherein step a) further includes varying the rate of mist generation.

17. The method of claim 1 wherein step a) includes varying the rate of mist generation and step e) includes varying the rate of condensing the vapor.

18. The method of claim 1 wherein said biocide solution may comprise water, biocides, hydrogen peroxide, alcohol, organic compounds and their mixtures, peracetic acid, vinegar, organic acids, ozone liquid, oils and their blends, fuels and their blends, petroleum distillates, kerosene, chlorine compounds, or combinations thereof.

19. The method of claim 1 wherein said evaporation gas comprises air, nitrogen, carbon dioxide, inert gases, or combinations thereof.

20. The method of claim 1 wherein after step, b) said evaporation gas is discharged at a high velocity relative to the mist creating a forced post convective evaporation region at a mist discharge point in the evaporator enclosure.

21. The method of claim 1 further including evaporating the condensed vapor cloud after the step f).

22. The method of claim 1 wherein step f) further includes providing a discharge stream in addition to the condensed vapor cloud with controlled portions of components of pure vapor, nano and sub-micron droplets of the mist, whereby additional applications are provided.

23. The method of claim 1 wherein the step of dispersing the condensed vapor cloud achieves 5-log to 6-log kill above 0.7 g/m3 of HP injected mass concentration for *G. Stearothermophilus* (spores) in Tyvek pouches.

24. A method for decontaminating a volume and its contents comprising the steps of:
   a. generating a mist of ultrafine droplets comprised of a biocide solution;
   b. generating an evaporation gas;
   c. the mist is a low momentum mist produced by an atomizer means, and the mist and the evaporation gas are premixed to form a premixed mixture;
   d. mixing the mist with the evaporation gas in an evaporator enclosure and providing a residence time sufficient to evaporate the mist;
   e. producing a vapor inside the evaporator enclosure from the evaporated mist;
   f. condensing a proportion of the vapor after discharge from an exit of the evaporator enclosure and forming a condensed vapor cloud; and
   g. dispersing the condensed vapor cloud throughout the volume to be decontaminated.

25. A method for decontaminating a volume and its contents comprising the steps of:
   a. generating a mist of ultrafine droplets comprised of a biocide solution;
   b. generating an evaporation gas;
   c. mixing the mist with the evaporation gas in an evaporator enclosure and providing a residence time sufficient to evaporate the mist;
   d. producing a vapor inside the evaporator enclosure from the evaporated mist and providing a high humidity vapor level inside the evaporator enclosure;
   e. condensing a proportion of the vapor after discharge from an exit of the evaporator enclosure and forming a condensed vapor cloud; and
   f. dispersing the condensed vapor cloud throughout the volume to be decontaminated.

26. A method for decontaminating a volume and its contents comprising the steps of:
   a. generating a mist of ultrafine droplets comprised of a biocide solution and providing an ultrasonic device having multiple misting jets containing recesses;
   b. generating an evaporation gas;
   c. producing a warm high-speed air discharge to evaporate biocide solution remaining in the recesses and exhausting the evaporated biocide solution;
   d. mixing the mist with the evaporation gas in an evaporator enclosure and providing a residence time sufficient to evaporate the mist;
   e. producing a vapor inside the evaporator enclosure from the evaporated mist;
   f. condensing a proportion of the vapor after discharge from an exit of the evaporator enclosure and forming a condensed vapor cloud; and
   g. dispersing the condensed vapor cloud throughout the volume to be decontaminated.

27. A method for generating and dispersing a condensed vapor cloud from liquid inputs including the steps of:
   a. generating a stream of mist droplets comprised of a liquid;
   b. generating a stream of an evaporation gas;
   c. introducing the stream of mist droplets and the stream of the warm evaporation gas in an evaporator enclosure causing the stream of mist droplets and the warm evaporation gas to mix turbulently with a residence time of the stream of mist droplets to evaporate the mist droplets and produce an evaporated mist;
   d. producing a high humidity vapor inside the evaporator enclosure from the evaporated mist;
   e. condensing the high humidity vapor and forming the condensed vapor cloud upon discharge from the evaporator enclosure via an outlet from the evaporator enclosure; and
   f. dispersing the condensed vapor cloud into a volume.

28. The method for generating and dispersing a condensed vapor cloud from liquid inputs including the steps of:
   a. generating a stream of mist droplets comprised of a liquid;
   b. generating a stream of an evaporation gas;
   c. introducing the stream of mist droplets and the stream of the warm evaporation gas in an evaporator enclosure causing the stream of mist droplets and the warm evaporation gas to mix turbulently with a residence time of the stream of mist droplets to evaporate the mist droplets and produce an evaporated mist;
   d. producing a high humidity vapor inside the evaporator enclosure from the evaporated mist;
   e. condensing the high humidity vapor and forming the condensed vapor cloud upon discharge from the evaporator enclosure via an outlet from the evaporator enclosure; and
   f. dispersing the condensed vapor cloud into a volume and providing air exchange devices below the outlet of the evaporator enclosure and exchanging and redistributing air below the outlet whereby a volume comprising multiple rooms receives distribution of the condensed vapor cloud.

* * * * *